United States Patent
Berger et al.

(10) Patent No.: US 9,662,215 B2
(45) Date of Patent: May 30, 2017

(54) SINTERABLE AND/OR FUSIBLE CERAMIC MASS, PRODUCTION AND USE THEREOF

(71) Applicant: Bundesrepublik Deutschland, vertreten durch das Bundesministerium fuer Wirtschaft und, Berlin (DE)

(72) Inventors: Georg Berger, Panketal (DE); Andrea Spitzer, Berlin (DE); Dagmar Nicolaides, Mahlow (DE); Jens Guenster, Berlin (DE); Heidi Marx, Berlin (DE)

(73) Assignee: Bundesrepublik Deutschland, Vertreten durch das Bundesministerium fuer Wirtschaft und Technologie, Dieses Vertreten durch den Praesidenten der BAM, Bundesanstalt fuer Materialforschung und—Pruefung, Berlin (DE)

( * ) Notice: Subject to any disclaimer, the term of this patent is extended or adjusted under 35 U.S.C. 154(b) by 0 days.

(21) Appl. No.: 14/778,910

(22) PCT Filed: Feb. 12, 2014

(86) PCT No.: PCT/EP2014/052733
§ 371 (c)(1),
(2) Date: Sep. 21, 2015

(87) PCT Pub. No.: WO2014/146831
PCT Pub. Date: Sep. 25, 2014

(65) Prior Publication Data
US 2016/0058558 A1    Mar. 3, 2016

(30) Foreign Application Priority Data

Mar. 21, 2013   (DE) ......................... 10 2013 102 917

(51) Int. Cl.
*C04B 35/22* (2006.01)
*A61F 2/30* (2006.01)
(Continued)

(52) U.S. Cl.
CPC ............ *A61F 2/30771* (2013.01); *A61F 2/28* (2013.01); *A61L 27/10* (2013.01); *A61L 27/12* (2013.01);
(Continued)

(58) Field of Classification Search
CPC .......... C04B 14/366; C04B 2235/3212; C04B 35/22; C04B 35/195
See application file for complete search history.

(56) References Cited

U.S. PATENT DOCUMENTS

| | | | | |
|---|---|---|---|---|
| 4,652,534 A | * | 3/1987 | Kasuga | ............... C03C 10/0018 433/201.1 |
| 4,871,384 A | * | 10/1989 | Kasuga | ................... A61L 27/12 501/5 |

(Continued)

FOREIGN PATENT DOCUMENTS

| | | |
|---|---|---|
| CN | 1153150 A | 7/1997 |
| CN | 101228096 A | 7/2008 |

(Continued)

OTHER PUBLICATIONS

German Office Action mailed Nov. 6, 2014 in DE 10 2013 102 917.5.

(Continued)

*Primary Examiner* — Noah Wiese
(74) *Attorney, Agent, or Firm* — Dicke, Billig & Czaja, PLLC

(57) ABSTRACT

A sinterable and/or fusible ceramic mass is disclosed, having a long-term stable compound of crystalline phases of apatite, wollastonite, titanite and optionally cristobalite, which is (Continued)

stabilized by a glass phase, and a production process therefor. The ceramic mass can be obtained by sintering a mixture comprising at least the constituents $SiO_2$, $CaO$, $P_2O_5$, $MgO$, $CaF_2$ and $TiO_2$, on their own or in combination with at least one alkali oxide, the alkali oxide being chosen from $NaO_2$ and $K_2O$. The invention further relates to uses of the sintered material in the form of shaped articles for strengthening, cleaning, roughening or polishing surfaces of medical implants or as a final prosthesis.

24 Claims, 3 Drawing Sheets

(51) Int. Cl.

| | |
|---|---|
| *A61L 27/10* | (2006.01) |
| *A61L 27/12* | (2006.01) |
| *C03C 3/112* | (2006.01) |
| *C03C 10/00* | (2006.01) |
| *C03C 10/16* | (2006.01) |
| *C04B 35/447* | (2006.01) |
| *C04B 35/468* | (2006.01) |
| *C04B 35/626* | (2006.01) |
| *C04B 35/653* | (2006.01) |
| *C09K 3/14* | (2006.01) |
| *B24C 11/00* | (2006.01) |
| *B82Y 30/00* | (2011.01) |
| *B24C 1/06* | (2006.01) |
| *B24C 1/08* | (2006.01) |
| *A61L 31/02* | (2006.01) |
| *C03C 4/00* | (2006.01) |
| *A61F 2/28* | (2006.01) |
| *C04B 35/14* | (2006.01) |
| *C04B 35/64* | (2006.01) |

(52) U.S. Cl.
CPC .......... *A61L 31/026* (2013.01); *A61L 31/028* (2013.01); *B24C 1/06* (2013.01); *B24C 1/08* (2013.01); *B24C 11/00* (2013.01); *B82Y 30/00* (2013.01); *C03C 3/112* (2013.01); *C03C 4/0007* (2013.01); *C03C 10/00* (2013.01); *C03C 10/16* (2013.01); *C04B 35/14* (2013.01); *C04B 35/22* (2013.01); *C04B 35/447* (2013.01); *C04B 35/468* (2013.01); *C04B 35/6262* (2013.01); *C04B 35/64* (2013.01); *C04B 35/653* (2013.01); *C09K 3/1427* (2013.01); *A61F 2002/2835* (2013.01); *A61F 2002/30906* (2013.01); *C04B 2235/3212* (2013.01); *C04B 2235/3236* (2013.01); *C04B 2235/3454* (2013.01); *C04B 2235/36* (2013.01); *C04B 2235/445* (2013.01); *C04B 2235/5427* (2013.01); *C04B 2235/5436* (2013.01); *C04B 2235/5445* (2013.01); *C04B 2235/5454* (2013.01); *C04B 2235/6567* (2013.01); *C04B 2235/661* (2013.01); *C04B 2235/668* (2013.01); *C04B 2235/80* (2013.01); *C04B 2235/94* (2013.01); *C04B 2235/96* (2013.01)

(56) References Cited

U.S. PATENT DOCUMENTS

| | | | |
|---|---|---|---|
| 7,704,907 B2 | 4/2010 | Guenther et al. | |
| 2004/0023784 A1 | 2/2004 | Yu et al. | |

FOREIGN PATENT DOCUMENTS

| | | |
|---|---|---|
| DE | 301764 | 10/1993 |
| JP | S61 158841 | 7/1986 |
| KR | 920000150 | 1/1992 |
| WO | 2012/137158 | 10/2012 |

OTHER PUBLICATIONS

German Office Action mailed Apr. 15, 2015 in DE 10 2013 102 917.5.
German Decision to Grant mailed Jul. 1, 2015 in DE 10 2013 102 917.5.
Deepak K. Pattanayak, et al. "Apatite Wollastonite-Titanium Biocomposites: Synthesis and In Vitro Evaluation", Jan. 30, 2006.
Chengtie Wu et al., "Incorporation of Titanium into Calcium Silicate Improved their Chemical Stability and Biological Properties", Published Oct. 29, 2007 in Wiley InterScience.
Ortega-Lara W et al., "In Vitro Bioactivity of Wollastonite-titania Materials Obtained by Sol-gel Method or Solid State Reaction", Published Aug. 13, 2008.
International Search Report mailed May 15, 2014 for PCT/EP2014/052733.
German Office Action mailed Nov. 19, 2013 in 10 2013 102 917.5.
Kokubo, T. (1991): Bioactive Glass-ceramics; Properties and Applications; Biomaterials, 12: 155-163.
Berger, G, et al. (1989): Clinical application of surface reactive apatite/wollastonite containing glass-ceramics. in: XV. Int. Congress on Glass, Leningrad, USSR, 3.-7.7.1989, vol. 3a: 120-126.
Berger, G, et al. (1984): In vitro characterization of bioactivity of glass-crystalline implant material using AUGER electron spectroscopy; physica status solidi (a), 85 (1): 9-13.

* cited by examiner

SINTERABLE AND/OR FUSIBLE CERAMIC MASS, PRODUCTION AND USE THEREOF

CROSS REFERENCE TO RELATED APPLICATION

This Utility Patent Application claims priority under 35 U.S.C. §371 to International Application Serial No. PCT/EP2014/052733, filed Feb. 12, 2014, which claims the benefit of German Patent Application No. 10 2013 102 917.5, filed Mar. 21, 2013; which are both incorporated herein by reference.

BACKGROUND

The invention relates to the field of sinterable and/or fusible ceramic masses, hereinafter termed ceramic masses, and shaped articles comprising ceramic masses, in particular in the field of bioactive or bioreactive bone replacements, i.e. a ceramic mass which acts to produce a direct bone contact free of connective tissue, with long-term stability, and a production and construction process therefor.

The term "ceramic mass" as used in this connection should be understood to mean an inorganic non-metallic substance, both in sintered, fired form, as well as in the form of a prepared material for sintering or firing. A ceramic shaped article is typically moulded from a raw mass at room temperature, for example a slip or a paste, and solidified by a high temperature sintering process. The preparation of a material for sintering may also include a first sintering step and subsequent grinding of the sintered material, for example, so that the ground material is then reused for the production of a slip or a paste from which a green body is formed. The green body can result in a sintered glass-ceramic, for example. This preparation may also include grinding previously fused glass. Further, it is possible for the molten glass to undergo a heat treatment so that—in accordance with conventional glass-ceramic processes—a crystallization occurs in the glass matrix.

The ceramic mass may be either a granulate which is used directly after appropriate pre-treatment to replace natural bone material or to supplement a bone in a living organism. Likewise, however, the ceramic mass may be processed to form a shaped article which, after suitable pre-treatment, completely replaces a bone in a living organism. Applicable processing procedures also additionally include additive manufacturing processes, for example what is known as 3D printing and other rapid prototyping processes, and optional subsequent separate sintering steps or even impregnation or colonization of the structures obtained with living cells.

Known bioactive/bioreactive glass-ceramics or ceramic masses with long-term stability predominantly consist of apatite and wollastonite. They can be prepared as sintered glass-ceramic (Kokubo [1]) or by traditional glass-ceramic processes (Berger et al [2]). Pure hydroxyapatite materials, which a priori are considered to be bioactive and have long-term stability, cannot be produced by any manner, especially as printed shaped articles, and are generally not strong enough to be used as a bone substitute material. In this context, a "bone substitute with long-term stability" or a "composite with long-term stability", as opposed to a resorbable material or a resorbable material composite, should be understood to mean a material which is not resorbed and not replaced by natural bone, but is substantially preserved during the service period which, for example, corresponds to the typical lifetime of the respective organism (vertebrate, man). Its solubility in the living organism or under physiological conditions of a cell and/or tissue culture is thus extremely low. This is shown by the fact that over the entire service period an interfacial surface of the material on which natural bone can accumulate is preserved in the organism in a continuous remodelling process, or the interfacial surface has an abrasive action in a technical application.

In particular, the solubility of known products based on glass-ceramics which exclusively contain the major crystalline phases apatite and wollastonite is still too high. If the solubility is reduced by the addition of $Al_2O_3$, $ZrO_2$ or $TiO_2$, then the resistance of the material under physiological conditions or in physiological solution is increased as a function of the quantity of additive, but this decreases the rate of formation of connective tissue-free direct bone contact because these substances ($Al_2O_3$, $ZrO_2$, $TiO_2$) are deposited and separate layers are formed [3].

BRIEF DESCRIPTION OF THE DRAWINGS

The accompanying drawings illustrate embodiments and, together with the description, serve to explain the principles of the invention.

DETAILED DESCRIPTION OF THE DRAWINGS

Figure 1:
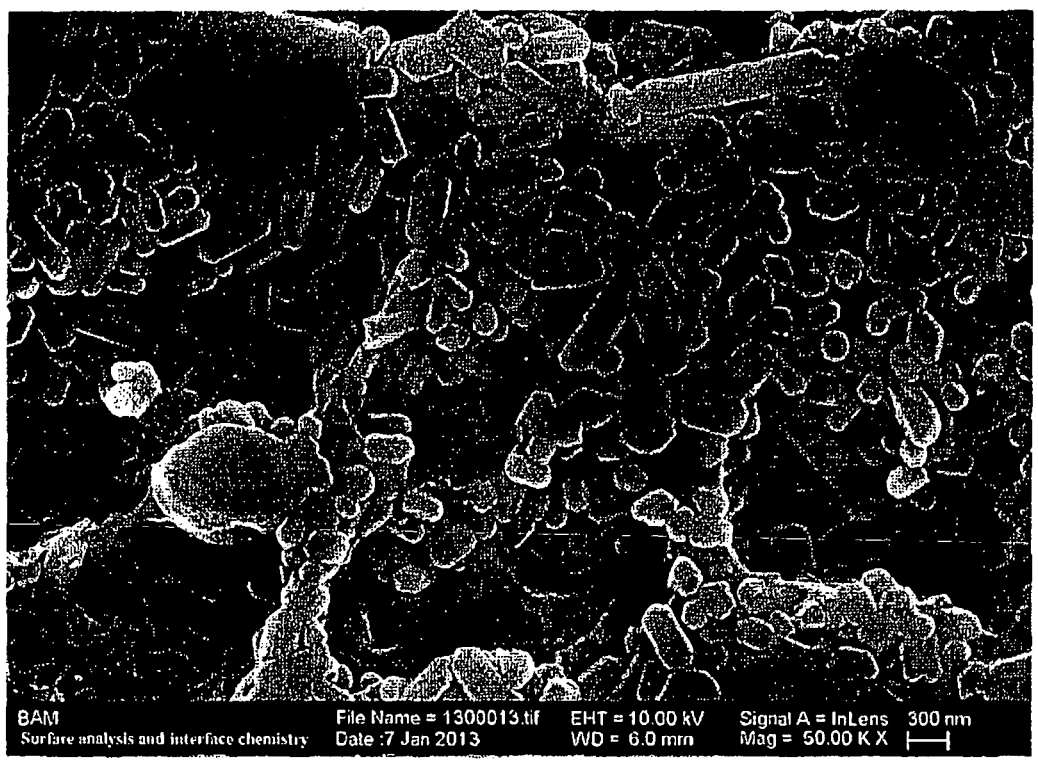
FIG. 1 shows a scanning electron microscope image of the heat treated material.

Against this background, a ceramic mass in accordance with claim 1, a process for the production of this ceramic mass in accordance with claim 5, uses of the ceramic mass or shaped articles obtained therefrom in accordance with claims 20 to 23, and a shaped article in accordance with claim 24 are proposed.

Further embodiments, modifications and improvements will become apparent from the following description and the accompanying claims.

In accordance with one embodiment, a ceramic mass is provided which comprises a composite of crystalline phases of apatite, wollastonite and titanite with long-term stability which is stabilized by a glass phase. In particular, the ceramic mass itself is characterized in that it is sinterable and/or fusible.

An advantage of this embodiment arises from the fact that the crystalline phases described are embedded in a stable manner in a common glass phase which is at least partially soluble in physiological media, thus offering advantageous anchoring possibilities for ingrowing cells and the accumulation of natural bone matter without the ceramic mass dissolving or being resorbed into the body, for example. This advantageously results in excellent osseointegration or a high degree of bone contact.

In accordance with one embodiment, a ceramic mass is provided which further comprises cristobalite in addition to said major crystalline phases of apatite, wollastonite and titanite.

An advantage of this embodiment arises from the fact that all of the crystalline phases described are embedded in a stable manner in a common glass phase, the ceramic mass is highly stable in physiological media and it has excellent osseointegration or a high degree of bone contact.

In accordance with one embodiment, a ceramic mass is provided which is characterized in that the ceramic mass comprises $SiO_2$, $CaO$, $P_2O_5$, $MgO$, $CaF_2$ and $TiO_2$, alone or in combination with at least one alkali metal oxide selected from $Na_2O$ and $K_2O$.

Advantages of this embodiment are that the solubility of the glass phase is achieved by the stoichiometric ratios of said substances, thus obtaining an advantageously high degree of bone contact.

In this context, the term "stoichiometric components" should be understood to mean the quantities or ratios by weight of the cited substances, wherein the stoichiometric ratios of the cited oxides or calcium fluoride may be obtained by weighing the various starting materials. As an example, the contribution of a desired quantity of the substance calcium, potassium or sodium and the corresponding salt of oxalic acid may be obtained by weighing.

In another embodiment, a ceramic mass is provided wherein the proportion of the glass phase in the ceramic mass after sintering is less than 25% by weight, preferably less than 10% by weight.

An essential advantage of the small proportion of the glass phase referred to is the increased stability of the sintered ceramic mass in physiological media, in particular in the presence of serum and upon colonization with living cells, in particular during osseointegration.

In accordance with a further embodiment, a process for the production of a sinterable and/or fusible ceramic mass is provided, which comprises the following steps:

providing a mixture comprising at least the components $SiO_2$, $CaO$, $P_2O_5$, $MgO$, $CaF_2$ and $TiO_2$, alone or in combination with at least one alkali metal oxide selected from $Na_2O$ and $K_2O$;

comminuting the mixture;

sintering or annealing the comminuted mixture in a first heat treatment step to form a first mass, wherein the sintering or annealing is carried out at a temperature in the range 650° C. to 800° C., in particular at 720° C., over a period of at least 1 hour, preferably over a period of 8 to 24 hours;

grinding the first mass;

slurrying the ground first mass to form a slip;

forming a green body from the slip;

sintering the green body in a second heat treatment step, wherein the sintering of the green body is carried out at a temperature in the range 850° C. to 1200° C., in particular 920° C. to 1150° C., over a period of at least 18 hours to 24 hours.

Advantages of this production process are the possibility of providing a sinterable and/or fusible ceramic mass which is adapted for the production of bone substitute material and artificial bone. A particular advantage of the production process is the provision of free-flowing powders and granulates which are particularly suitable for additive manufacturing processes.

In another embodiment, sintering or annealing of the first heat treatment step is preceded by melting the comminuted mixture at a melting temperature below 1650° C., in particular below 1620° C. In accordance with an exemplary embodiment, melting can be carried out, for example in a crucible produced, for example, from platinum/rhodium.

This offers particular advantages for obtaining a finely crystalline microstructure of apatite, wollastonite, titanite and cristobalite, embedded in a glass matrix or a glass-ceramic comprising a fine crystalline microstructure of apatite, wollastonite, titanite and cristobalite.

In accordance with a further embodiment of the production process, the mixture which is provided comprises 35-45% by weight of $SiO_2$; 25-35% by weight of $CaO$, 10-15% by weight of $P_2O_5$; 2-4% by weight of $MgO$, 4-6% by weight of $CaF_2$ and 4-10% by weight of $TiO_2$ and may contain 0.001-5% by weight of $Na_2O$ and/or 0.001-0.2% by weight of $K_2O$.

Advantages of this embodiment arise from synchronous precipitation of the apatite, wollastonite, titanite and optional cristobalite crystalline phases using the composition described herein, without the appearance of deposits of titanium oxide-rich layers after completion of the sintering process which, for example, prevent a direct bone contact in the recipient.

In accordance with a further embodiment of the production process, a mean diameter of the particles in order to obtain the ceramic mass of mixed ingredients is 0.5-3000 μm, preferably 0.5-3 μm; in particular 2-10 μm; 10-100 μm; 50-1000 μm or 300-3000 μm.

Advantages of this embodiment arise from the uniform appearance and/or the homogeneous distribution of the precipitated apatite, wollastonite, titanite and typically additional cristobalite crystalline phases. The uniform distribution of these crystallites results in high strength of the shaped articles obtained which is independent of a major direction of loading.

In accordance with a further embodiment, the proposed production process comprises filling a sintering mould. The sintering mould is adapted to the size and shape of the required final shaped article such that no further processing is required following sintering. This is in particular possible because, using the proposed composition of the starting materials, deposits of layers, for example titanium oxide-rich layers, no longer have to be removed, because they no longer occur. The sintered shaped article can therefore be used immediately, for example as a bone substitute.

In accordance with a further embodiment of the proposed process for the production of a sinterable and/or fusible ceramic mass, sintering is carried out in two unpressurized stages.

Advantages of this embodiment arise from a substantially simplified process protocol. As an example, a sintering step may comprise sintering a powder by powder spray sintering.

In accordance with a further embodiment, sintering is carried out in a first unpressurized step at a temperature of 650° C. to 800° C., in particular at 720° C., for a time period of 1 to 48 hours, in particular for a time period of 24 hours, and in a second unpressurized step at a temperature of 850° C. to 1200° C., in particular at 920° C. to 1150° C. for a time period of 1 to 48 hours, in particular for a time period of 24 hours.

Advantages of this embodiment arise because the advantageous phase composition of the materials obtained in view of the preferred degree of bone contact and the preferred mechanical strength is obtained at a comparatively small technological outlay.

In accordance with a modification of the latter two embodiments, the second sintering step is preceded by comminuting the ceramic mass obtained after the first sintering step.

Advantages arise in particular from a homogeneous structure in terms of pore size distribution and the uniform distribution of the various crystalline phases, as well as a resultant isotropic strength for the resulting shaped articles. This offers particular advantages as regards the suitability of the shaped articles obtained for their intended applications.

In accordance with a further embodiment, a weight ratio of the sum of the starting materials $SiO_2$, CaO, $P_2O_5$, MgO and $CaF_2$ to the weight of the $TiO_2$ used is set at a ratio of 8:1 to 20:1. Details of advantageous embodiments can be found in Table 5 below.

In a further embodiment, a process is proposed for the production of a sinterable and/or fusible ceramic mass which comprises a composite with long-term stability of crystalline phases of apatite, wollastonite, titanite and optionally also cristobalite stabilized by means of a glass phase. This production process is characterized by a weight ratio of the sum of $SiO_2$, CaO and $P_2O_5$ in the mixture of the starting materials for the ceramic mass to that containing $TiO_2$ in the mixture of the starting materials of 7:1 to 20:1. This weight ratio means that advantageously, the formation of a titanium oxide-rich phase deposit can be avoided.

In accordance with a further embodiment of the production process, the green body is moulded in layers or using an additive process employing a slip of the comminuted starting materials or a slip of the comminuted ceramic mass obtained after a first sintering step.

Additive processes typically require a distribution of the mean particle sizes in the powder, granulate or slip employed which is adapted to the respective process. Due to either a largely freely adjustable size distribution and/or mean particle sizes obtained by the comminution steps or a mean particle size set by suitable spray sintering, this results in the possibility of adapting the respective particle size to the preferred additive process. Thus, the known advantages of additive processes can be exploited. As an example, a slip can be processed by a suitable printing process. This, for example, allows the ceramic mass described to be used for the production of three-dimensional shaped articles which are built up in layers.

In accordance with a further embodiment, grinding of the first sintered mass is carried out without additives. This has the advantages of reduced time requirements and decreased costs.

In accordance with a further embodiment, the sinterable and/or fusible ceramic mass is proposed for use as a blasting abrasive for medical implants, with a mean grain size of the blasting abrasive in the range 50-5000 µm, preferably in the range 50 µm to 1000 µm.

The disadvantages of previous blasting abrasives, for example corundum, can be overcome because of the advantageous physiological compatibility and high degree of bone contact. The blasted surfaces do not have to undergo complicated cleaning; blasting material which might be left in any undercuts in the surface might even improve ingrowth into a treated surface.

In accordance with a further embodiment, the sinterable and/or fusible ceramic mass in the form of a castable mass described above is proposed for use in a slip casting process, wherein a mean grain size of the particles dispersed in the castable mass is in the range 0.5 µm to 7 µm, preferably in the range 0.5 µm to 3 µm.

Advantages arise from the suitability of the ceramic mass for additive production processes.

In another embodiment, the sinterable and/or fusible ceramic mass described above is provided for use in the solidification, cleaning, roughening or polishing of surfaces of medical implants, wherein the ceramic mass is in the form of a shaped article, and a mean expansion of the shaped article in one spatial direction is in the range 0.25 µm to 1 cm, in particular in the range 0.5 µm to 500 µm.

Advantages arise from the universal applicability of the ceramic mass, be it as an abrasive material, a fine blasting agent or a polishing agent for metal or polymeric surfaces or for the surfaces of shaped articles comprising a composite material.

In accordance with a further embodiment, the sinterable and/or fusible ceramic mass described above and a shaped article obtained therefrom is provided for use as a abrasive material for a medical implant or an endoprosthesis.

From the advantageous physiological compatibility and high degree of bone contact, the disadvantages of conventional abrasive materials such as corundum can be avoided. The surfaces treated with the abrasive materials no longer have to undergo cleaning; blasting material which might be left in any undercuts in the surface might even improve ingrowth into a treated surface.

In accordance with a further embodiment, the sinterable and/or fusible ceramic mass described above is provided for the treatment of a metallic surface.

Advantages arise both from the strength of the ceramic shaped articles as well as from the excellent biocompatibility of the ceramic mass or, as the case may be, of shaped articles produced therefrom.

In accordance with a further embodiment, the sinterable and/or fusible ceramic mass described above is provided for use as a castable mass for slip casting, wherein the ceramic mass comprises discrete particles with a mean diameter of the individual particles in the range 0.5 µm to 7 µm, preferably in the range of 0.5 µm to 3 µm.

Advantages arise from the fact that slip casting-based processes allow the maximum freedom in the design of the shape and size of the green body.

In accordance with a further embodiment, the sinterable and/or fusible ceramic mass described above is provided for use for the production of a press granulate, wherein the press granulate has a mean granulate particle size of 0.5 µm to 500 µm.

Advantageously, the described ceramic mass is suitable for the production of a wide range of granulate particle sizes. Thus, application-specific granulates can be provided which have the advantageous properties of the sintered ceramic mass described herein.

In accordance with a further embodiment, the sinterable and/or fusible ceramic mass described above is provided for the production of a free-flowing powder for an additive manufacturing process, in which the free-flowing powder has a mean powder particle size of 10 µm to 125 µm.

Free-flowing powders are of great importance both for wet and for dry bed technologies for reasons of effective use of the materials and for reasons of process economics. The freely adjustable mean particle size of the free-flowing powder allows for application-specific process optimization.

In accordance with a further embodiment, the sinterable and/or fusible ceramic mass described above is provided in the form of an implant granulate and for replacing or supplementing natural bone material, wherein the implant granulate has a mean particle size of 300 µm to 3000 µm.

Advantages arise from the particular suitability of such an implant granulate for oral surgery and orthodontics, for example.

In accordance with a further embodiment, the sinterable and/or fusible ceramic mass as described above is provided as blasting material for surface treatment, wherein the ceramic mass has a mean particle size of 50 µm to 5000 µm, for example 50 µm to 2500 µm.

As described, the average particle size is freely adjustable. Thus, the sinterable and/or fusible ceramic mass described herein can be processed using various technologies or, as the case may be, the shaped articles produced therefrom may be used in various fields, for example as bone substitute material, for bone augmentation, the production of scaffold and support structures, as biocompatible filling material and as artificial bone.

In accordance with a further embodiment, a shaped article is provided comprising a sinterable and/or fusible ceramic mass as described herein, wherein the shaped article is selected from: a microparticle, a bead, a granulate, a polyhedron, a plate, a discus, an ellipsoid, a rod, a tube, a cylinder, a cone, a bone-shaped structure or a part or a section of at least one of said shaped articles.

The variety of available forms described encompasses a very wide range of preferred applications. Particularly preferred applications are those that require good biocompatibility, a good degree of bone contact, rapid osseointegration and/or good cell and tissue compatibility, especially for mammalian cells and mammalian tissue.

With regard to possible fields of application, the materials and shaped articles described may be considered for use in the fields of veterinary medicine, human medicine, medical research and related areas of surface treatment.

The embodiments described above may be combined in any manner.

In particular, FIG. 1 shows the fine crystalline structure of the microstructure obtained by the proposed heat treatment (see the "300 nm" scale bar at the edge of the image) of the crystals embedded in a glass matrix. This glass-ceramic was obtained from the fusible ceramic mass AWT7-o.K—Si (see Table 5, bottom row).

Starting from compositions which produce a ceramic mass, in particular a glass-ceramic, with the major crystalline phases apatite and wollastonite (AW), completely surprisingly, a hitherto unusually high addition of a $TiO_2$ component produces a third major crystalline phase consisting of a titanium silicate or titanite. Typically, from the proposed compositions, it is possible to precipitate out a fourth major crystalline phase, namely cristobalite if a further sintering step is carried out after sintering and solidification of the ceramic mass. The precipitation of two additional major crystalline phases, i.e. the appearance of said third (titanite) and fourth (cristobalite) major crystalline phases, brings about a reduction in the proportion of the glass phase with respect to the ceramic mass. The proportion of the glass phase in the proposed ceramic mass compared with a glass-ceramic based on apatite and wollastonite is reduced to only approximately 10% by weight. This also contributes to an increase in the chemical resistance and/or long-term stability of the proposed ceramic mass in physiological solution or in a living organism.

It is generally understood that a "ceramic mass" is a composition of starting materials, for example, a mixture of powders. The composition or, as the case may be, the powder mixture is processed after thorough admixing which may, for example, be carried out by way of milling and/or homogenization in order to form a green body which, as a result of a sintering procedure, forms a shaped article or a solid ceramic mass with all of the properties described herein. The sintered ceramic mass comprises at least the said four major crystalline phases and a glass phase.

In spite of the described reduction in the proportion of the glass phase to the ceramic mass which is obtained, the proportion of glass phase with respect to the proposed ceramic mass, however, is still sufficiently high for 3D shaped articles with a sufficient mechanical stability to be capable of being printed from granulated, fused glass-ceramic mass following unpressurized sintering (see Table 1) for use, for example, as a bone substitute.

TABLE 1

Strength of AWT7-o.K-Si 3D printed shaped articles

| Grain size [μm] | Strength [MPa] |
| --- | --- |
| 25-45 | 4.1 |
| 45-100 | 2.6 |

Clearly, shaped articles produced from the ceramic mass and/or the glass-ceramic mass produced by traditional ceramic processing under pressure have a higher mechanical strength when the shaped article is produced than the unpressurized shaped articles produced as mentioned above. This is demonstrated, for example, by the shaped articles produced in the form of tablets shown as an exemplary embodiment (see Table 2).

TABLE 2

Strengths of AWT7-o.K-Si 3D pressed articles

| Grain size [μm] | Strength [MPa] |
| --- | --- |
| 0.5-3.0 | 38.4 |
| 1.5-35.0 | 120.7 |

The skilled person is aware that when high proportions of titanium oxide are added to ceramic masses, titanium oxide-rich layers appear on the apatite and wollastonite glass-ceramics obtained, which severely restrict the suitability of the glass-ceramics obtained as a bone substitute material. In this context, $TiO_2$ proportions of 4% to 5% by weight are already considered to be high; $TiO_2$ proportions of 7% by weight are considered to be very high. Consequently, $TiO_2$ proportions of above 4% to 5% by weight, and also of 7% by weight and more are usually avoided in order to prevent the precipitation of titanium oxide-rich layers on the surface of a sintered shaped article.

However, it has been shown that, in accordance with the proposed process, an addition of $TiO_2$ of 5% by weight or more to the system in order to obtain apatite and wollastonite glass-ceramics can avoid the conventional disadvantages of the occurrence of deposits of titanium oxide-rich layers. Surprisingly, in fact, it has been shown that in addition to apatite or wollastonite, titanite and cristobalite are also present in the sintered ceramic mass while deposits of titanium oxide-rich layers are still absent when, for example, 7% by weight or more of $TiO_2$, typically up to 10% by weight is added to the ceramic mass. As a result, the degree of bone contact of shaped articles obtained in this manner is increased compared with those with deposits of titanium oxide-rich layers, and at the same time, the long-term stability of the material is increased.

Under the proposed conditions, these four crystalline phases: apatite, wollastonite, titanite and cristobalite, are synchronously precipitated, advantageously preventing the deposition of a $TiO_2$-rich layer. The ceramic mass obtained is characterized by a high bioactivity. The term "bioactivity" in this context should be understood to mean bony attachment of the respective ceramic in the absence of connective tissue. In particular, this should be understood to mean the ingrowth or accretion of bone into or on the surface of the sintered ceramic mass or a bone replacement material comprising the proposed ceramic mass or an implant or shaped article comprising the ceramic mass or an endoprosthesis having a surface treated therewith, i.e. connective tissue-free osseointegration into the organism.

The skilled person is aware that the phase composition can be varied widely using various process technologies, in particular by selecting the initial size of the shaped article or, as the case may be, its individual particulate components, even though the stoichiometric composition or even the initial charge might well be the same. This will be illustrated in Table 3 in the following example.

The starting material was the composition AWT7-o.K—Si.

TABLE 3

| Initial form | Approximate % by weight | | | | |
|---|---|---|---|---|---|
| | Apatite | Wollastonite | Titanite | Cristobalite | Glass phase |
| Glass-ceramic (particle volume >1 cm³) 24 h/720° C., 24 h/920° C. | 15 | 18 | 22 | 18 | 27 |
| Sintered glass-ceramic Ground material 25-45 μm 24 h/720° C., 24 h/920° C. | 8 | 16 | 17 | 20 | 39 |
| Pressed shaped article Ground material $d_{50}$ = 1.4 μm 24 h/720° C., 24 h/920° C. | 12 | 21 | 23 | 14 | 30 |
| Pressed shaped article Ground material $d_{50}$ = 12.8 μm 24 h/720° C., 24 h/920° C. | 7 | 20 | 19 | 21 | 33 |
| 3D printed shaped article Ground material $d_{50}$ = 45-100 μm 24 h/720° C., 24 h/920° C. | 5 | 17 | 21 | 23 | 33 |
| 3D printed shaped article Ground material $d_{50}$ = 25-45 μm 24 h/720° C., 24 h/920° C. | 7 | 20 | 25 | 14 | 34 |
| Glass-ceramic (particle volume >1 cm³) 14 days/720° C., 13 days/920° C. | 14 | 14 | 20 | 19 | 34 |

The scientific basis for this variation is that the volumes for surface crystallization will be strongly influenced by the selected process conditions.

Precipitation of the four major crystalline phases during the sintering process is also possible if the individual crystallites (major crystalline phases), or some or all four major crystalline phases are used in the comminuted form. The term "apatite" as used herein means a crystalline compound in accordance with the general formula $Ca_5[(F, Cl, OH)|(PO_4)_3]$; the term "cristobalite" means a crystalline compound with general formula $SiO_2$; the term "titanite" means a crystalline compound in accordance with the formula $CaTi[O|SiO_4]$; and the term "wollastonite" means a crystalline compound with formula $CaSiO_3$ or $Ca_3[Si_3O_9]$. Clearly, these crystalline compounds may incorporate trace deposits of other elements which are present during crystal formation from the starting materials as inevitable trace elements. The starting materials present in the ground material used were of purity grade "p.a." and were thus substantially free of impurities.

The skilled person is also aware that the phase composition can be varied widely during sintering by applying different temperature profiles, even though the stoichiometric composition and even the starting charge may be identical. This is demonstrated in the experimental data summarized in Table 4.

TABLE 4

Proportions of crystalline phases and glass, as approximate % by weight

| AWT7-o.K-Si samples Sintering variations | Apatite | Wollastonite | Titanite | Cristobalite | Glass phase |
|---|---|---|---|---|---|
| Glass | | | | | 100 |
| 950° C./1 h | 12 | 12 | 20 | 14 | 42 |
| 1000° C./1 h | 15 | 15 | 27 | 13 | 31 |
| 1050° C./1 h | 16 | 16 | 31 | 15 | 22 |
| 1100° C./1 h | 12 | 13 | 17 | 16 | 42 |
| 1150° C./1 h | 12 | 16 | 23 | 24 | 24 |
| 1200° C./1 h | 16 | 10 | 20 | 14 | 40 |

Figure 2:
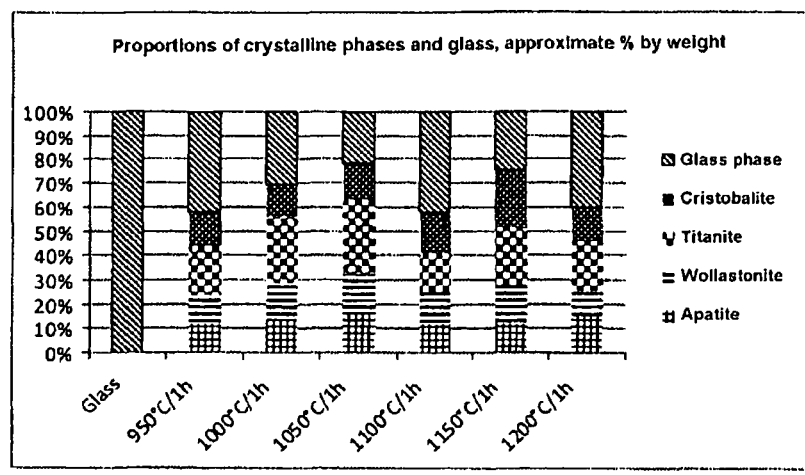
FIG. 2 shows the proportions of the crystalline phases and glass as a function of the heat treatment of Table 4, as a block diagram.

A graphical representation of the values listed in Table 4 is shown in FIG. 2.

The user is thus provided with a glass-ceramic mass with long-term stability which can be used either directly in the form of a granulate as a bone substitute, or can be processed using different process technologies into shaped articles which also have properties relevant to bone replacement. In addition, the ceramic material can be used for various types of surface treatment of endoprostheses or implants, in particular metallic shaped articles.

An example of such a surface treatment is blasting in the manner of sand blasting in order to roughen a surface of the endoprosthesis, wherein the blasting abrasive used in this case comprises the proposed ceramic material. Another example of the surface treatment using the glass-ceramic mass described here is shot peening. In the case of such an application, the blasting abrasive used for shot peening comprises compact shaped articles of sintered ceramic mass, preferably in the form of beads. Another example of a surface treatment with the aid of the glass-ceramic mass described herein or with shaped articles therefrom is polishing. In this case, the glass-ceramic mass or abrasive material formed therefrom is used as a polishing agent. Abrasive materials used for polishing may advantageously have a polyhedral shape, for example in the form of prisms or cubes, or a spherical shape or an ellipsoidal shape. Ready-to-use polishing agents may, for example, comprise particles of different shapes and sizes, wherein the shape, the size and the mixing ratio of the various particles or abrasive materials are determined by the respective characteristics of the objects to be polished. Preferably, the abrasive materials are used for abrading and/or polishing metal parts of endoprostheses.

The common advantage of all of the proposed types of surface treatment of an endoprosthesis by contact with a shaped article comprising a ceramic mass of the proposed composition which has undergone at least two sintering steps is that residues of the ceramic mass which remain on the surface of the endoprosthesis support osseointegration of the endoprosthesis, whereas the corundum which is normally employed as a blasting abrasive reduces the biocompatibility of the surface which has been treated or blasted with the blasting abrasive.

The proposed ceramic mass represents a novel combination of materials which is characterized by a homogeneous distribution of the apatite, wollastonite, titanite and cristobalite crystalline phases in a glass phase.

In addition to opening up new scientific horizons, this material is therefore suitable both as a bone substitute and as shaped articles, as well as for use as a stable and improved blasting abrasive for the treatment of implant surfaces. The sintered corundum used in the prior art suffers from the disadvantage that corundum particles which become anchored in blasted metal parts, e.g. in hip joint endoprosthesis shafts, prevent direct connective tissue-free bone contact.

Ceramic masses in the form of glass-ceramics with various compositions and properties were prepared and tested; the starting mixtures used to obtain the glass-ceramics are summarized in the following Table 5.

TABLE 5

Stoichiometric composition of AWT variations (as a % by weight)

| Sample | $SiO_2$ | CaO | $P_2O_5$ | $K_2O$ | $Na_2O$ | MgO | $CaF_2$ | $TiO_2$ |
|---|---|---|---|---|---|---|---|---|
| AW [2] | 44.30 | 31.89 | 11.21 | 0.20 | 4.60 | 2.80 | 5.00 | — |
| AWT5 | 42.19 | 30.37 | 10.68 | 0.19 | 4.38 | 2.67 | 4.76 | 4.76 |
| AWT7 | 41.40 | 29.80 | 10.48 | 0.19 | 4.30 | 2.62 | 4.67 | 6.54 |
| AWT9 | 40.64 | 29.26 | 10.28 | 0.18 | 4.22 | 2.57 | 4.59 | 8.26 |
| AWT11 | 39.91 | 28.73 | 10.10 | 0.18 | 4.14 | 2.52 | 4.51 | 9.91 |
| AWT7-o.KNa | 43.17 | 31.07 | 10.94 | — | — | 3.41 | 4.87 | 6.54 |
| AWT7-o.K | 42.29 | 30.44 | 10.70 | — | 1.91 | 3.34 | 4.78 | 6.54 |
| AWT7-o.K-Si | 39.60 | 32.04 | 11.26 | — | 2.01 | 3.52 | 5.03 | 6.54 |

The starting materials, $SiO_2$, $CaCO_3$, $Ca_3(PO_4)_2$, MgO, $CaF_2$ $TiO_2$; $Na_2CO_3$; $K_2CO_3$ were weighed, homogenized for one hour in a tumbler mixer and then melted at 1550° C. to 1600° C. for three hours. The low-viscosity melt was cast onto a steel plate or sintered, depending on the subsequent processing.

Figure 3:
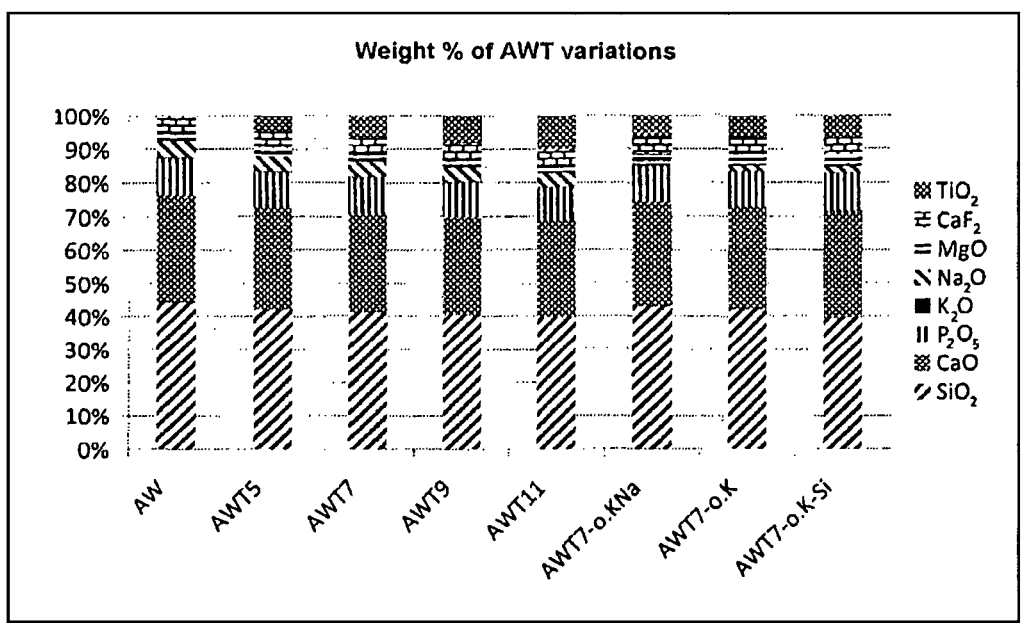
FIG. 3 shows the stoichiometric compositions of the AWT variations from Table 5, as a block diagram.

The abbreviation AW used in the table refers to the known prior art apatite/wollastonite [2] and AWT as used in the present description and the claims refers to the sintering of shaped apatite-wollastonite-titanite. The numeral after the abbreviation AWT describes the proportion by weight of further added components. The abbreviation "AWT-o.K" or "AWT-o.KNa" stands for mixtures which are free of potassium or of potassium and sodium. The data in Table 5 are also shown in FIG. 3 as a block diagram, which indicates the compositional variations.

Thus, the proposed composition provides a combination of crystalline inorganic materials which fulfil the requirements for a bone replacement with long-term stability in an appropriate manner. In particular, the low solubility, respectively the high chemical resistance of the material under physiological conditions, an excellent processability into shaped articles and the high strength of these shaped articles, as well as direct, connective tissue-free ingrowth behaviour, i.e., the bioactivity of the proposed ceramic mass, represent an optimal combination of features which recommend the ceramic mass for application in the most varied aspects of bone replacement material applications. Accordingly, the ceramic material is proposed for use as a bone defect filling material and for bone augmentation, as a bone substitute or as shaped articles, as a blasting abrasive and as shaped articles for roughening and/or shot peening and/or polishing of endoprostheses. Specific embodiments relate to the treatment of the surface of jaw implants, knee and hip joint implants, in particular the roughening of a hip joint endoprosthesis shaft.

In summary, therefore, a sinterable and/or fusible ceramic mass comprising a proposed composite of crystalline phases of apatite, wollastonite, titanite and optional cristobalite with long-term stability is provided which is stabilized by a glass phase, and a production process therefor is also provided. The ceramic mass is obtained by sintering a mixture comprising at least the components $SiO_2$, CaO, $P_2O_5$, MgO, $CaF_2$ and $TiO_2$, alone or in combination with at least one alkali metal oxide, wherein the alkali metal oxide is selected from $Na_2O$ and $K_2O$. Clearly, in providing a glass phase or in providing starting materials which are known to those skilled in the art for the formation of a glass phase, a starting material comprising the ground crystalline phases of apatite, wollastonite, titanite and cristobalite is used to produce the ceramic mass. Further embodiments relate to uses of the sintered material in the form of shaped articles for the solidification, cleaning, roughening or polishing of surfaces of medical implants or as an endoprosthesis.

While specific embodiments have been illustrated and described herein, the scope of the present invention encompasses modifying the embodiments shown appropriately without departing from the scope of the present invention. The following claims are a first, non-binding attempt to define the invention in general.

LIST OF REFERENCES

[1] Kokubo, T. (1991): Bioactive Glass-ceramics; Properties and Applications; Biomaterials, 12: 155-163.

[2] Berger, G; Sauer, R; Steinborn, G; Wihsmann, F G; Thieme, V; Köhler, St; Dressel, H. (1989): Clinical application of surface reactive apatite/wollastonite containing glass-ceramics. in: XV. Int. Congress on Glass, Leningrad, USSR, 3.-7.7.1989, Volume 3a: 120-126.

[3] Berger, G; Atzrodt, V. (1984): In vitro characterization of bioactivity of glass-crystalline implant material using AUGER electron spectroscopy; physica status solidi (a), 85 (1): 9-13.

What is claimed is:

1. A ceramic mass comprising a composite with long-term stability of crystalline phases of apatite, wollastonite, cristobalite and titanite, which is stabilized by a glass phase.

2. The ceramic mass according to claim 1, wherein the ceramic mass comprises $SiO_2$, CaO, $P_2O_5$, MgO, $CaF_2$ and $TiO_2$, alone or in combination with at least one alkali metal oxide selected from $Na_2O$ and $K_2O$.

3. The ceramic mass according to claim 2, comprising at least 5% by weight of $TiO_2$.

4. The ceramic mass according to claim 1, wherein the proportion of the glass phase in the ceramic mass after sintering is less than 25% by weight.

5. A process for the production of the ceramic mass of claim 1, comprising:
   providing a mixture comprising at least the components $SiO_2$, CaO, $P_2O_5$, MgO, $CaF_2$ and $TiO_2$, alone or in combination with at least one alkali metal oxide selected from $K_2O$ and $Na_2O$;
   comminuting the mixture;
   sintering the comminuted mixture to produce a first sintered mass, wherein sintering is carried out at a temperature in the range 650° C. to 800° C. over a period of 1 hour to 24 hours;
   grinding the sintered mixture;
   slurrying the ground mixture to form a slip;

forming a green body from the slip; and sintering the green body in a second sintering step, wherein sintering of the green body is carried out at a temperature in the range 850° C. to 1200° C. over a period of at least 18 to 24 hours, wherein the mixture comprises:

35-45% by weight of $SiO_2$; 25-35% by weight of CaO, 10-15% by weight of $P_2O5$; 2-4% by weight of MgO, 4-6% by weight of $CaF_2$ and 6.5-9.9% by weight of $TiO_2$; and optionally 0.001-0.2% by weight of $K_2O$ and/or 0.001-5% by weight of $Na_2O$.

6. The process according to claim 5, wherein sintering of the comminuted mixture is preceded by fusing the comminuted mixture at a melting temperature of less than 1620° C.

7. The process according to claim 5, wherein a mean diameter of particles of the components in order to obtain the ceramic mass is in the range selected from 0.5-3000µm.

8. The process according to claim 5, further comprising: filling a sintering mould with the comminuted mixture.

9. The production process according to claim 5, wherein the sintering is carried out in two unpressurized steps.

10. The process according to claim 5, wherein the step of sintering the comminuted mixture is carried out in a first unpressurized step at a temperature of 650° C. to 800° C. for a time period of one hour to 24 hours and in a second unpressurized step at a temperature of 850° C. to 1200° C. for a time period of at most about 24 hours.

11. The process according to claim 5, wherein a weight ratio of the sum of the components $SiO_2$, CaO, $P_2O_5$, MgO and $CaF_2$ in the mixture to the mass of $TiO_2$ contained in the mixture is 8:1 to 20:1.

12. The process according to claim 5, wherein a weight ratio of the sum of the components $SiO_2$, CaO and $P_2O5$ in the mixture to the mass of $TiO_2$ contained in the mixture is 7:1 to 20:1.

13. The process according to claim 5, wherein shaping of the green body is carried out layer by layer or by using an additive process.

14. The process according to claim 5, wherein the first sintered mass is ground without additives.

15. A process for finishing a medical implant, the process comprising blasting the medical implant with an abrasive is made of the ceramic mass according to claim 1, and wherein the mean grain size of the abrasive is in the range 50-1000 µm.

16. A production process comprising slip casting a castable mass comprising dipersed particals made of a ceramic mass according to claim 1, wherein the mean particle size of the dispersed particles is in the range 0.5 to 7 µm.

17. A production process comprising cleaning, roughening or polishing surfaces of a medical implant with at least one shaped article of a ceramic mass according to claim 1, wherein a mean expansion of the at least one shaped article in a spatial direction is in the range 50 µm to 1 cm.

18. A production process comprising abrading a medical implant, an endoprosthesis, or a metallic surface with an abrasive material comprising a ceramic mass according to claim 1.

19. The production prrocess according to claim 16, wherein the castable mass comprises discrete dispersed particles having a mean diameter in a range from 0.5 µm to 3 µm.

20. Use of a ceramic mass according to claim 1 for the production of a press granulate, wherein the press granulate has a mean granulate particle size of 0.5 µm to 500 µm.

21. Use of a ceramic mass according to claim 1 for the production of a free-flowing powder for an additive manufacturing process, wherein the free-flowing powder has a mean powder particle size of 10 µm to 125 µm.

22. Use of a ceramic mass according to claim 1 as an implant granulate for replacing or augmenting natural bone material, wherein the implant granulates have a mean particle size of 300 µm to 3000 µm.

23. Use of a ceramic mass according to claim 1 as a blasting material for surface treatment, wherein the ceramic mass has a mean particle size of 50 µm to 5000 µm.

24. A shaped article comprising a ceramic mass according to claim 1, wherein the shaped article is selected from: a microparticle, a bead, a granulate, a polyhedron, a plate, a discus, an ellipsoid, a rod, a tube, a cylinder, a cone, a bone-shaped structure or a part or a section of at least one of said shaped articles.

* * * * *